United States Patent [19]

Bordow

[11] 4,085,737
[45] Apr. 25, 1978

[54] DEVICE AND TECHNIQUE FOR MINIMIZING RISK OF CONTAMINATION BY BLOOD SAMPLE

[76] Inventor: Richard A. Bordow, 6114 Terryhill Dr., La Jolla, Calif. 92037

[21] Appl. No.: 720,624

[22] Filed: Sep. 3, 1976

[51] Int. Cl.² .......................................... A61B 19/00
[52] U.S. Cl. .............................. 128/2 F; 128/218 R; 128/DIG. 5
[58] Field of Search .......... 128/2 G, 2 F, 215, 218 R, 128/218 N, 218 NV, 218 S, 218 M, 272, 276, DIG. 5

[56] References Cited

U.S. PATENT DOCUMENTS

| | | | |
|---|---|---|---|
| 2,551,414 | 5/1951 | Burnside | 128/218 N |
| 2,731,012 | 1/1956 | Henderson | 128/215 |
| 2,772,677 | 12/1956 | Ulert et al. | 128/215 |
| 2,896,622 | 7/1959 | Huttermann | 128/218 M |
| 3,162,195 | 12/1964 | Dick | 128/DIG. 5 |
| 3,382,865 | 5/1968 | Worrall, Jr. | 128/2 F |
| 3,734,080 | 5/1973 | Petterson et al. | 128/DIG. 5 |

FOREIGN PATENT DOCUMENTS 1,153,676  3/1958  France ............................ 128/218 N

*Primary Examiner*—John D. Yasko
*Attorney, Agent, or Firm*—Perry J. Saidman

[57] ABSTRACT

A method and apparatus for reducing the risk of contamination of individuals who handle a blood sampling needle and syringe subsequent to the taking of the sample. The apparatus includes a substantially tubular needle guard having an open end and a closed end and adapted to be fitted about the needle of the blood sampling syringe. A fluid impervious stopper or seal is affixed to the inner wall of the needle guard at a position intermediate its ends. The enclosed chamber between the seal and the closed end of the needle guard has been evacuated to a subatmospheric pressure. After the blood sample has been drawn, the user places the needle guard about the needle in such a fashion that the tip of the needle penetrates the seal so as to be enclosed within the vacuum chamber. A small amount of air or an air and blood mixture will then be drawn into the vacuum chamber from the syringe, and the entire unit may be thereaffter safely handled. The technician performing the blood analysis may utilize the needle guard to remove the needle from the syringe as a further precaution against contamination.

17 Claims, 4 Drawing Figures

U.S. Patent      April 25, 1978      4,085,737
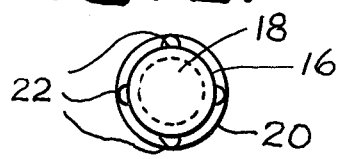
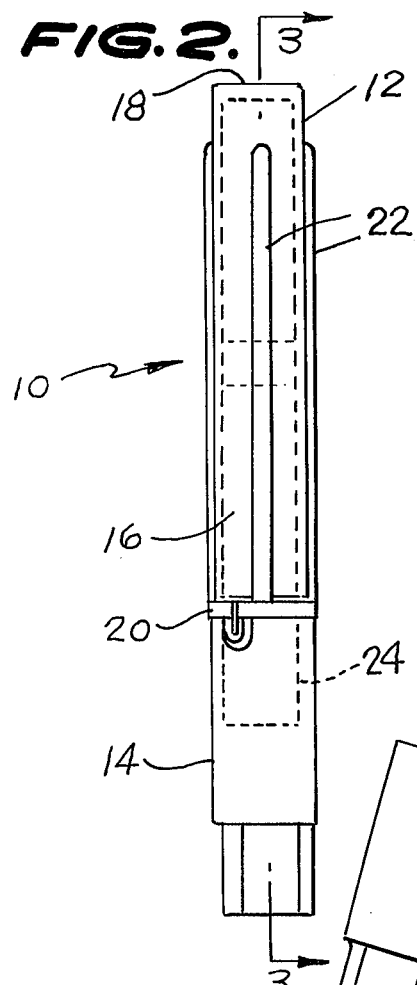
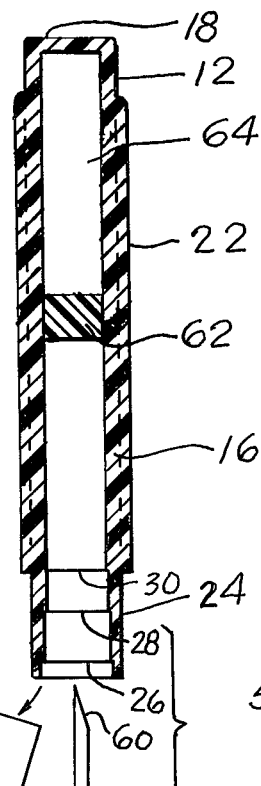
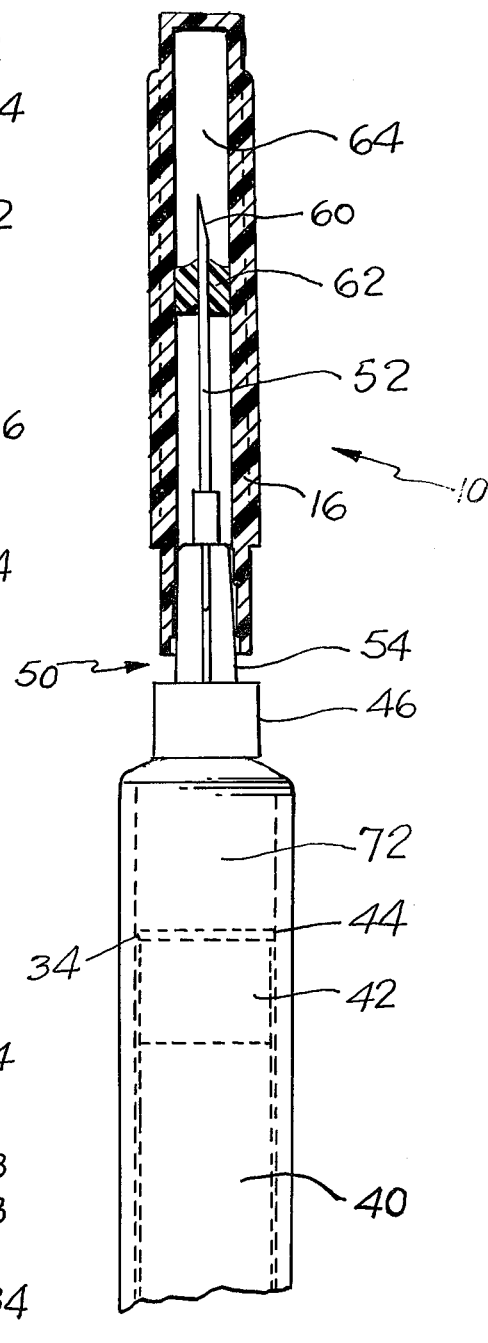

DEVICE AND TECHNIQUE FOR MINIMIZING RISK OF CONTAMINATION BY BLOOD SAMPLE

BACKGROUND OF THE INVENTION

1. Field of the Invention

The present invention is related to blood sampling techniques and devices and, more particularly, is directed towards a method and apparatus for substantially reducing the risk of contamination of handlers of a blood sampling syringe and needle by the sampled blood.

2. Description of the Prior Art

Blood gas aspiration is a technique widely practiced by nurses, physicians, medical students and respiratory therapists in order to obtain important data for proper management of an ill patient. For example, in patients suffering from diseases of the lungs or heart, it is important to know the oxygen content of the blood, which may be determined by blood gas analysis of arterial blood.

Such blood is obtained from the patient using a conventional hypodermic syringe. The use of a conventional needle and syringe in blood gas aspiration techniques unfortunately lends itself to possible serious contamination of the individual obtaining the blood by the patient's blood. This risk of contamination extends to those individuals, such as technicians or the like, who most subsequently handle the blood-filled syringe and/or needle during analysis.

There are several steps during the performance of the blood gas aspiration technique where the risk to the syringe handler of contamination by the patient's blood may be identified as greatest. One of those instances occurs in connection with the manual purging of air from the syringe which is required as a result of the inevitable aspiration of air into the syringe when the sample is being taken. It is quite important that air not be allowed to contaminate the blood sample, which would distort the results of the gas analysis. Therefore, as a practical matter, after the sample has been drawn, the taker of the sample generally must eject some blood through the needle prior to sending the sample-filled syringe to the laboratory to be analyzed, in order to purge all air from the sample. The amount of blood which is ejected during this purging process necessarily depends upon the skill and technique of the user. The practical result is, however, that a careless individual may undesirably expose his fingers, either directly or through a piece of gauze, to the ejected, possibly contaminated blood of the patient.

Immediately following the purging of air from the syringe as above-described, the open end of the needle of the syringe must be pushed into a small rubber stopper or the like preparatory to sending the sample-filled syringe to a laboratory for analysis. If a person is careless, there is a chance that the open end of the needle will touch or prick his fingers, thereby creating another opportunity for contamination.

As an alternative to pushing the needle into a stopper, the person sampling the blood may choose to remove the needle from the syringe altogether prior to sending the blood-filled syringe to the lab. In this procedure, after the needle is removed, the open end of the syringe must be plugged with a rubber syringe cap, and the proximity of the user's hands to the patient's blood sample is again perilously close.

Still another opportunity for contamination occurs after the laboratory technician receives the blood-filled syringe for analysis. The technician must either remove the stoppered needle, which is generally done by grasping the base of the needle assembly at a point adjacent the end of the blood-filled syringe, or, alternatively, the technician must manually remove the syringe cap, which also places his hands in close proximity to the blood. In either event, the chances of getting blood on his hands is great, which, obviously, increases the risk of contamination.

It is therefore apparent that there is a great need for some type of device and technique which can minimize or at least substantially reduce the risk of contamination from a diseased patient's blood for those individuals, from the person initially drawing the blood sample to the person doing the blood analysis, who must handle the blood-filled hypodermic syringe.

OBJECTS AND SUMMARY OF THE INVENTION

It is therefore a primary object of the present invention to provide a method and apparatus for minimizing or at least substantially reducing the risk of contamination of individuals handling a syringe having a blood sample of an ill patient.

Another object of the present invention is to provide a method for reducing the risk of contamination of the person drawing the sample of blood when the air must be purged from the sample.

A further object of the present invention is to provide a technique for minimizing the risk of blood contamination of an individual who draws a blood sample from an ill patient when the hypodermic syringe must be stoppered for transmittal to a laboratory for subsequent analysis.

A still further object of the present invention is to provide a method and apparatus for minimizing the risk of blood contamination of a technician who must handle the blood-filled syringe and needle for analysis.

A still further object of the present invention is to provide a device which may be easily incorporated into existing arterial blood sampling kits and which may be utilized to reduce or minimize the risk of contamination of handlers of the hypodermic syringes therein contained after a blood sample has been drawn.

An additional object of the present invention is to provide an inexpensive and easily manufactured device for utilization with existing arterial blood sampling kits which substantially lessens the risk of contamination of any individual handling the hypodermic syringe after the blood sample has been drawn.

A still further object of the present invention is to provide a modified blood gas aspiration technique which automatically ensures the removal of any air aspirated during the sampling of the blood.

The foregoing and other objects are attained in accordance with one aspect of the present invention through the provision of a syringe needle guard which comprises a substantially tubular member having an open end and a closed end, and means positioned intermediate the open end and the closed end for defining a substantially fluid impermeable chamber adjacent the closed end of the tubular member. The fluid impermeable chamber has preferably been evacuated to a subatmospheric pressure, and the means positioned intermediate the open and closed ends of the tubular member preferably comprises means for sealably engaging the needle of the syringe after a blood sample has been taken thereby. The engaging means preferably comprises a fluid impermeable seal which is affixed to the inner wall of the tubular member.

In accordance with another aspect of the present invention, there is provided in combination with a blood sampling syringe having a needle with an open end, apparatus which comprises means for covering the open end of the needle and means for drawing a small amount of fluid from the syringe into the covering means through the open end of the needle. The drawing means comprises an evacuated chamber within which the open end of the needle is situated, the covering means including an enclosed portion which defines the evacuated chamber. The covering means more particularly comprises a tubular member having an open end and a closed end, and means positioned within the tubular member for sealing a portion thereof. The sealing means preferably comprises a fluid impermeable seal affixed to the inner wall of the tubular member, the seal in a preferred embodiment comprising a rubber stopper.

In accordance with yet another aspect of the present invention, there is provided in a blood sampling method wherein blood is drawn from a patient through an open-ended needle into a syringe, a technique for reducing the risk of contamination by the sampled blood of individuals who subsequently handle the needle and/or syringe, which comprises the step of enclosing the open end of the needle of the syringe in an evacuated chamber. More particularly, the step of enclosing the open end of the needle of the syringe in an evacuated chamber includes the steps of providing a tubular syringe needle guard having an open end and a closed end, affixing fluid impermeable stopper means through the needle guard intermediate its open and closed ends, evacuating air from the portion of the needle guard between the stopper means and the closed end, and inserting the open end of the needle through the stopper means into the evacuated portion of the needle guard. The pressure in the evacuated portion is preferably subatmospheric in order to automatically draw a portion of air and/or blood into the evacuated chamber in order to purge the air from the blood sample prior to analysis.

BRIEF DESCRIPTION OF THE DRAWINGS

Various objects, features and attendant advantages of the present invention will be more fully appreciated as the same become better understood from the following detailed description thereof when considered in connection with the accompanying drawings, in which:

FIG. 1 is a top view of a preferred embodiment of the present invention;

FIG. 2 is a side plan view illustrating a preferred embodiment of the device of the present invention prior to use;

FIG. 3 illustrates a sectional view of the preferred embodiment of the device of the present invention taken along line 3—3 of FIG. 2, and illustrates a side plan view of the needle/syringe assembly utilized in conjunction with the present invention; and FIG. 4 is a view of the components illustrated in FIG. 3 in their final assembled state, ready for safe handling and transportation.

DETAILED DESCRIPTION OF THE PREFERRED EMBODIMENTS

Referring now to the drawings, wherein like reference numerals designated identical or corresponding parts throughout the several views, and more particularly to FIGS. 1 and 2 thereof, reference numeral 10 indicates generally a preferred embodiment of the present invention in the form of a tubular syringe needle guard, which is preferably formed of plastic.

The needle guard 10 is made in two parts, a needle enclosing portion 12 and a removable hollow cap portion 14. The needle enclosing portion 12 is comprised of a substantially cylindrical and hollow body 16 having a closed end 18 integrally formed thereon. At the distal end of body 16 is positioned a slightly enlarged diameter base portion 20. Radially extending along the periphery of body portion 16 may be formed a plurality of longitudinally placed reinforcing ribs 22, which also serve as finger assisting grips during handling of the needle guard 10.

As seen more particularly in FIG. 3, the lower end of the needle enclosing portion 12 of needle guard 10 terminates in a reduced diameter open end 24. The outer diameter of open end 24 is sized so as to frictionally receive and hold the hollow cap 14 thereon prior to use. The inner diameter of open end 24 is formed as a series of reduced diameter portions 26, 28 and 30, which are adapted to snugly engage the base 54 of the needle assembly 50, in a manner to be described in more detail hereinafter.

Still with reference to FIG. 3, a standard syringe is indicated generally by the reference numeral 32. Syringe 32 includes a tubular glass holder 34 which terminates in its working end in a centrally formed extension 36 having a through aperture 38 axially formed therein and in communication with the central hollow portion of holder 34, all of which is conventional.

As seen in FIG. 4, syringe 32 includes a conventional plunger 40 having a leading head 42, formed of a flexible rubber or the like, with an enlarged flange 44 for forming a fluid-tight seal with the inner surface of holder 34.

A cup-shaped, preferably plastic, needle assembly holder 46 is firmly secured to the end of glass holder 34 about the extension 36. On the inner surface of holder 46 are provided one or more integrally formed threads 48 for threadably receiving the needle assembly which is indicated generally by reference numeral 50.

Needle assembly 50 includes an axially extending hollow needle 52 which terminates in a beveled needle tip 60. The distal end of needle 52 is secured within a hollow base member 54, which is preferably comprised of a molded plastic. About the periphery of base 54 are a plurality of radially extending flanges 56 which serve as means for retaining the open end 24 of the needle guard 10 on the base portion 54 of the needle assembly 50. The diameters of flanged portions 26, 28 and 30 of the open end 24 of needle guard 10 are sized in conjunction with the flanges 56 so as to enable the base 54 first to be guided, as between flange portions 26 and 28, and then to be snap-fit, as between portions 28 and 30, into the open end 24 of guard 10.

The base 54 of needle assembly 50 further has formed at the lower portion thereof a flange 58 positioned about the periphery of its open end. Flange 58 serves as a means for retaining the needle assembly 50 within the holder 46. Base 54 may be screwed into holder 46 with, for example, a quarter or half turn, so as to be axially fixed therein. The base 54 must be rotated counterclockwise (unscrewed) in order to remove the needle assembly 50 from holder 46 once secured.

The foregoing sets forth a substantially conventional syringe, needle assembly, and syringe guard, the latter element being modified by the present invention in a manner to be explained hereinbelow.

A stopper or seal 62 is affixed to the inner wall of the needle enclosing portion 12 of the tubular syringe needle guard 10 at a position intermediate the open end 24 and closed end 18 thereof. The stopper or seal 62 may be formed of rubber, plastic, or other suitable fluid impermeable material, and is illustrated as being positioned at approximately the mid-length of tubular member 12. Stopper or seal 62 may be held in place by any suitable adhesive, or may simply be oversized so as to be substantially friction locked in place.

Between stopper 62 and the closed end 18 of tubular member 12 is defined a closed chamber 64. Subsequent to the installation of stopper 62, chamber 64 is preferably evacuated, by any conventional technique, to a subatmospheric vacuum which may be, for example, about −15mmHg. The subatmospheric chamber 64 serves, as will become more clear hereinafter, as an automatic suction to purge any accidentally aspirated air from the blood sample.

In operation, after the blood sample 72 has been drawn into the syringe 32 in the usual fashion, the person taking the sample removes the cap 14 from the needle guard assembly 10. Without disturbing the plunger 40 of the syringe 32, and with the needle 52 preferably in an upright position as illustrated in FIG. 3, the tubular member 16 is grasped near its upper end as viewed in FIG. 3 and is then lowered by the user about the needle 52 until the tip 60 thereof penetrates stopper 62 and comes to rest within vacuum chamber 64, as illustrated in FIG. 4. At this point, a small amount, perhaps one-half cubic centimeter, of air, or an air and blood mixture, will be drawn into the vacuum chamber 64, which serves to purge the blood sample 72 of possible air contaminants prior to analysis.

Furthermore, nothing further need be done to transmit the blood-filled syringe 32 to the laboratory, except for placement of the entire assembly in an ice-packed bag. That is to say, the risk of contamination inherent in the prior art steps of purging the sample of air and stoppering the needle have been obviated by the present invention technique which may be performed in but a single step, which may be broadly described as simply enclosing the open end 60 of the needle 52 within an evacuated chamber 64.

The arterial blood from the sample 72 will not spill on the user, since the only vent (tip 60) exhausts into a closed chamber 64. There is no risk of exposure to the open tip 60 of needle 52 since the entire assembly will be safely enclosed within the tubular body 16.

The laboratory technician who receives the final assembly as illustrated in FIG. 4 may simply grasp the needle guard 10 at the upper portion thereof, a substantial distance from the end 36 of the syringe 32, and may unscrew the needle assembly 50 utilizing the upper end of guard 10 as a handle. This reduces the chance of the technician accidentally spilling blood on himself from opening 38 of extension 36 once the needle assembly is removed. Once the asembly 50 is removed, the technician conventionally places the extension 36 of syringe 32 into a blood analysis machine and injects the blood sample thereinto.

While stopper 62 has been illustrated as positoned at the approximate midpoint of tubular member 16, it should be understood that it may be placed at any suitable position within the confines of tubular member 16 as engineering considerations may dictate. For example, for longer needles, it may be desirable to position stopper 62 closer to the end 18 of member 16, thereby providing a smaller vacuum chamber 64. Alternatively, for example, the positioning of stopper 62 may be selected to ensure that the flanges 56 of needle assembly 50 will be engaged by the reduced diameter inner guide flanges of open end 24 to assist the axial centering of needle 52 prior to engagement of the tip 60 by the stopper 62.

The particular thickness of stopper or seal 62 is also a matter of design choice. The important considerations are that it be sufficiently thick to support the necessary vacuum within chamber 64 as well as to provide a fluid-tight seal to keep blood and air therewithin. Seal 62 could be comprised of a fluid impervious membrane, or could have a centrally formed thinned or otherwise reduced resistance portion to facilitate the entry and passage of the needle therethrough.

The particular degree of vacuum in chamber 64 may also be selected to suit the desired purpose. For example, a higher degree of vacuum will ensure that a certain amount of blood will be drawn from sample 72 into chamber 64 to give a visual indication that the air has indeed been purged. Alternatively, the pressure within chamber 64 may be selected simply to permit the user to actuate plunger 40 once the guard 10 has been installed, which would allow manual purging of air from the sample 72 but without any risk of contamination, since any blood ejected would be contained within enclosed chamber 64.

It should be understood that the particular illustrated shape and design of the present invention were selected on the basis of providing a device and technique easily incorporated into existing arterial blood gas aspiration sampling kits. Clearly and obviously, numerous modifications and variations of the present invention are possible in light of the above teachings. The present invention may be utilized or practiced in any environment where it is desirable to minimize the potential hazards of blood contamination from hypodermic syringes. It is therefore to be understood that within the scope of the appended claims the invention may be practiced otherwise than as specifically described herein.

I claim as my invention:

1. In combination with a blood sampling syringe having a needle with an open end, apparatus which comprises means for covering said open end of said needle and means for drawing a small amount of fluid from said syringe into said covering means through said open end.

2. The apparatus as set forth in claim 1, wherein said drawing means comprises an evacuated chamber within which said open end of said needle is positioned.

3. The apparatus as set forth in claim 2, wherein said covering means includes an enclosed portion which defines said evacuated chamber.

4. The apparatus as set forth in claim 2, wherein said evacuated chamber is at a subatmospheric pressure.

5. The apparatus as set forth in claim 3, wherein said covering means comprises a tubular member having an open end and a closed end, and means positioned within said tubular member for sealing a portion thereof which defines said enclosed portion.

6. The apparatus as set forth in claim 5, wherein said sealing means comprises a fluid impermeable seal affixed to the inner wall of said tubular member.

7. The apparatus as set forth in claim 6, wherein said fluid impermeable seal comprises a rubber stopper.

8. A syringe needle guard, which comprises
a substantially tubular member having an open end and a closed end; and
means positioned intermediate said open end and said closed end for defining a substantially fluid impermeable chamber at subatmospheric pressure and adjacent said closed end of said tubular member.

9. The syringe needle guard as set forth in claim 8, wherein said means positioned intermediate said open end and said closed end comprises means for sealably engaging the needle of a syringe after a blood sample has been taken thereby.

10. The syringe needle guard as set forth in claim 9, wherein said engaging means comprises a fluid impermeable seal affixed to the inner wall of said tubular member.

11. The syringe needle guard as set forth in claim 10, wherein said fluid impermeable seal comprises a rubber stopper.

12. A technique for reducing the risk of contamination by sampled blood, which comprises the steps of taking a blood sample by drawing blood from a patient through an open-ended needle into a syringe, and enclosing the open end of the needle of the syringe in an evacuated chamber.

13. The technique as set forth in claim 12, wherein said enclosing step includes the step of inserting said open end of said needle through a fluid impermeable stopper means which defines the entrance to said evacuated chamber.

14. The technique as set forth in claim 12, wherein said enclosing step includes the steps of:
providing a tubular syringe needle guard having an open end and a closed end;
affixing fluid impermeable stopper means to said needle guard intermediate said open end and said closed end; and
inserting said open end of said needle through said stopper means into the portion of said needle guard between said stopper means and said closed end.

15. The technique as set forth in claim 14, further comprising the step, performed after said stopper means is affixed to said needle guard, of evacuating air from the portion of said needle guard between said stopper means and said closed end.

16. The technique as set forth in claim 15, wherein said step of evacuating air includes the step of reducing the pressure in said evacuated portion to subatmospheric.

17. Apparatus, which comprises:
a blood sampling syringe including a fluid holder, a hollow needle with an open end extending from one end of said holder, and a plunger movable in said holder to draw or expel fluid into or from said holder through said open end of said needle;
means for covering said open end of said needle; and
means for drawing a small amount of fluid from said fluid holder into said covering means through said open end.

* * * * *